(12) United States Patent
Ulbricht et al.

(10) Patent No.: US 6,515,039 B1
(45) Date of Patent: Feb. 4, 2003

(54) METHOD FOR THE PARALLEL AND COMBINATORY SYNTHESIS OF COMPOUNDS BOUND TO A CONTINUOUS POLYMERIC SOLID PHASE SUPPORTING MATERIAL

(75) Inventors: Mathias Ulbricht, Berlin (DE); Rudolf Volkmer-Engert, Berlin (DE); Lothar Germeroth, Berlin (DE); Holger Wenschuh, Berlin (DE)

(73) Assignee: Poly-An GmbH, Berlin (DE)

(*) Notice: Subject to any disclaimer, the term of this patent is extended or adjusted under 35 U.S.C. 154(b) by 0 days.

(21) Appl. No.: 09/530,457
(22) PCT Filed: Aug. 28, 1999
(86) PCT No.: PCT/EP99/06294
§ 371 (c)(1),
(2), (4) Date: Jun. 15, 2000
(87) PCT Pub. No.: WO00/12575
PCT Pub. Date: Mar. 9, 2000

(30) Foreign Application Priority Data

Aug. 28, 1998 (DE) .......................... 198 40 541

(51) Int. Cl.[7] .............................. C08F 2/46; C08F 2/50
(52) U.S. Cl. .................. 522/114; 522/113; 522/115; 522/116; 522/117; 522/118; 522/119; 522/120; 522/121; 522/122; 522/123; 522/124; 522/125; 522/129; 522/130; 522/64; 522/84; 522/86; 522/88; 522/87; 522/89
(58) Field of Search ................ 522/113–130, 84, 522/86, 88, 87, 89, 46

(56) References Cited

U.S. PATENT DOCUMENTS 4,908,405 A   3/1990   Bayer et al.

FOREIGN PATENT DOCUMENTS

DE   19643566      4/1998
WO   WO91/13098    9/1991

OTHER PUBLICATIONS

Kubota et al. Journal of Polymer Science: Polymer Ed. Letters, 19, 457–462 (1981).*
Derwent Abstract No. 98–189192/17 for Japanese Pat. Appl. No. 10045630.
Derwent Abstract No. 95–280934/37 for Japanese Pat. Appl. No. 07179531.
Derwent Abstract No. 92–070110/09 for Japanese Pat. Appl. No. 04016219.
Derwent Abstract No. 76–48519X/26 for Japanese Pat. Appl. No. 51052489.

* cited by examiner

Primary Examiner—James J. Seidleck
Assistant Examiner—Sanza K McClendon
(74) Attorney, Agent, or Firm—Kriegsman & Kriegsman

(57) ABSTRACT

The invention relates to a method for the parallel and combinatory synthesis of compounds bound to a continuous polymeric solid phase supporting material. According to the method, a continuous polymeric solid phase supporting material is prepared, the material comprising a matrix of a supporting polymeric material and graft copolymer chains covalently bound to the supporting matrix, the graft copolymer chains having reactive groups being able to react with organic compounds, thereby forming spatially defined reaction sites. The method then comprises the sequential spotting of synthesis building blocks or reagents at the various reaction sites on the continuous solid phase supporting material to yield a substrate library of compounds bound to the solid phase supporting material, whereby each reaction site on the continuous solid phase supporting material determines the composition of the synthesized compound, which is bound directly on the supporting matrix via the reactive groups of the graft polymer chain.

22 Claims, 1 Drawing Sheet

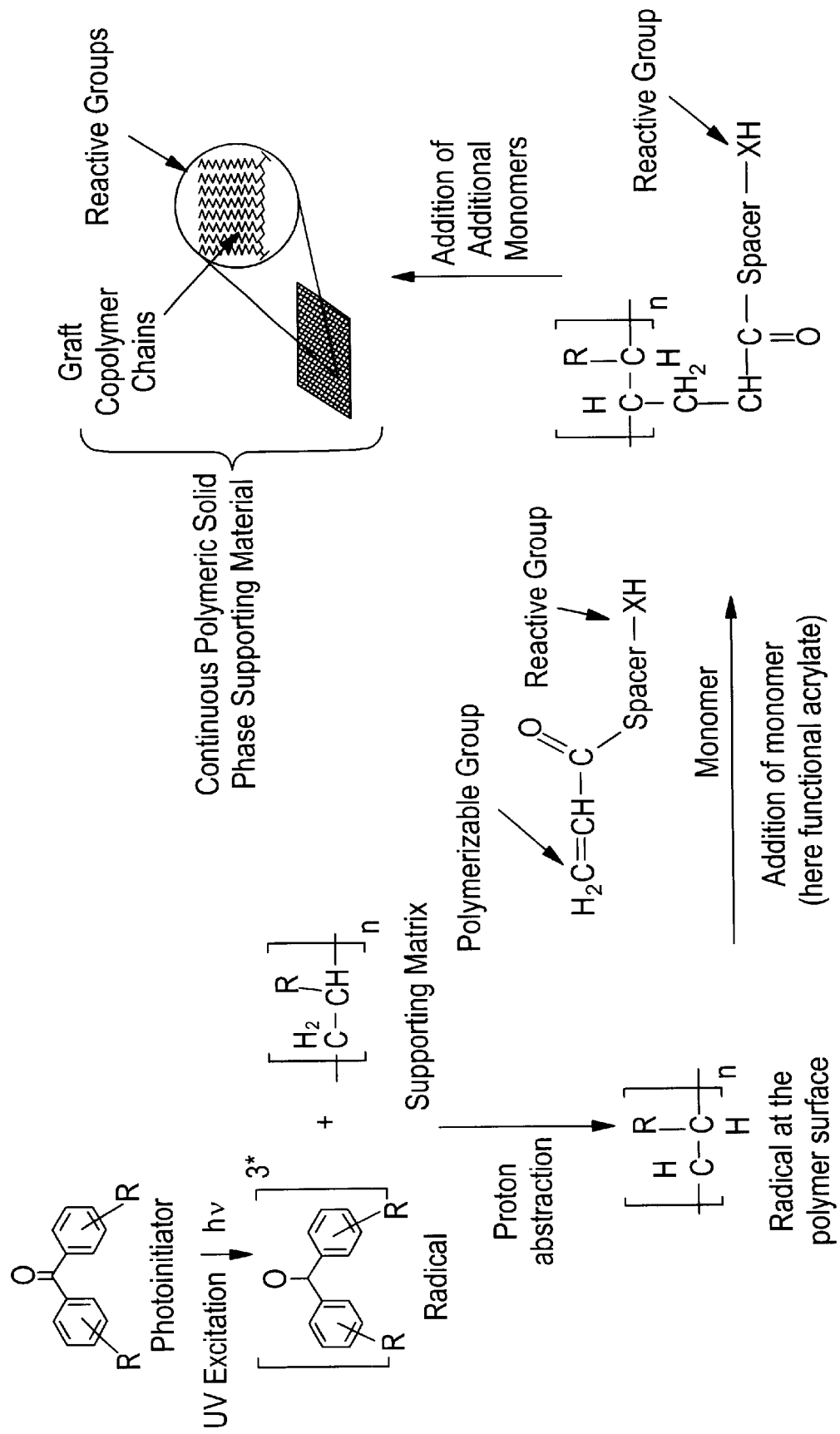

METHOD FOR THE PARALLEL AND COMBINATORY SYNTHESIS OF COMPOUNDS BOUND TO A CONTINUOUS POLYMERIC SOLID PHASE SUPPORTING MATERIAL

The invention concerns a method for the production of continuous polymeric solid phase supporting materials for simultaneous combinatory synthesis of organic compounds by means of SPOT synthesis technology, comprised of a polyolefin supporting matrix and individual chains of a graft copolymer, which are synthesized by heterogeneous photo-initiated graft copolymerization of acrylate, vinyl and allyl monomers on the entire surface of the supporting polymer and contain reactive hydroxyl, carboxyl, amino, mercapto, aldehyde or halogen groups, which can be utilized for additional derivatizing.

DESCRIPTION OF THE PRIOR ART

The chemical synthesis of compounds with the use of the concept of combinatory libraries has an important influence on the process of developing potential candidates for new therapeutic and diagnostic agents. Combinatory chemistry is a technique in which a large number of structurally different compounds are produced under comparable reaction conditions in a cost-favorable and time-efficient manner and can be subsequently introduced into biological testing by high-performance screening assays. The further development of Merrifield's solid phase synthesis strategy [Merrifield, R. B.: J. Am. Chem. Soc. 1963, 85, 2149], originally introduced for the synthesis of peptides, occupies a key position here. Since the use of excess reagents makes possible nearly complete reactions, and since the methodology can be easily automated and biological test systems can be applied directly onto polymeric surfaces, combinatory chemistry is preferably conducted in the solid phase.

The modification and further development of the original polystyrene supporting systems and the later-used polyamide systems [Atherton, E.; Clive, D. L. J.; Sheppard, R. C.; J. Am. Chem. Soc. 1975, 97, 6584] led to new polymers, such as, e.g., Tentagel and PEGA resins [Rapp, W.; Zhang, L.; Häbich, R.; Bayer, E. In Peptides 1988, (G. Jung & E. Bayer, Eds.) Walter de Gruyter, Berlin, New York, p.199; Meldal, M.; Tetrahedron Lett. 1992, 33, 3077]. These systems were increasingly utilized also for solid phase syntheses of non-peptide substances. Although spherical resin beads of various materials are broadly used, other physical forms such as small rods (polyethylene) or continuous surfaces (cellulose, cotton, glass, polyolefins) have led to new synthesis techniques.

The method of Spatially Addressable Combinatorial Libraries [Review: Pirrung, M. C.; Chem. Rev. 1997,97, 473] is such a synthesis concept. A decisive advantage of these substance libraries consists of the fact that the position at which a synthesized molecule is found on the polymer describes its composition. Thus, with the use of supporting materials that are suitable in format and structure, the application of compatible biological test systems can lead directly to information relative to the biological activity of the synthesized substances.

The form of appearance, the chemical and physical properties and the surface functionalization of the supporting materials thus act decisively on both the quality and efficiency of the synthesis as well as on compatibility with biological test systems.

The SPOT technology developed by Frank [Frank, R.; Tetrahedron, 1992, 48, 9217] for constructing peptides on planar cellulose surfaces makes particularly possible the efficient parallel construction of large numbers of peptide sequences. The method in which the reagents are pipetted to local addresses on the continuous support is further characterized by applicability of conventional screening assays, since the readout geometries of high-performance test systems are compatible with the planar supporting materials. Thus, for example, SPOT arrays could be utilized, in addition to classical epitope mapping, in order to discover optimal binding sequences of protein kinases or metal-binding peptides [Tegge, W.; Frank, R.; Hoffman, F., Dostmann, W. R. G.: Biochemistry 1995, 34,10569; Malin R.; Steinbrecher, R.; Jannsen, J.; Semmler, W.; Noll, B.; Johannsen B.; Frömmel, C.; Höhne, W.; Schenider-Mergener, J.: J. Am. Chem. Soc. 1995, 117,11821].

Based on the limited chemical and mechanical stability of the cellulose membranes, however, the technology has been previously limited, to the production of peptide sequences that are produced under relatively mild synthesis conditions.

Due to the structure of the chemically homogeneous support and the utilization of hydroxy groups as reactive groups, the permanent excess of hydroxy functions on the cellulose surface leads to the fact that selective or complete reactions cannot be achieved. This is a particular disadvantage for the generation of different linker constructs, which decisively limits the variety of possible reactions.

Several developments in the field of planar supporting materials could overcome the disadvantages of cellulose under certain conditions for SPOT synthesis, but have previously not been applied to the SPOT synthesis technique.

Thus, the patents of Berg et al. (WO 90/02749, WO 91/13098) and Batsberg et al. (WO 95/00533) describe the use of polyolefin films (preferably polyethylene). These were modified by gamma irradiation or by means of chemically initiated graft polymerization and homopolymerization of styrene from alcoholic solutions. Another chemical derivatization for introducing reactive groups followed. The supports produced in this way were used in reactors for peptide and oligonucleotide synthesis. In addition, solid-phase assay (ELISA) could be conducted.

Although the grafting of polystyrene chains is a logical further development of the classic Merrifield resin for a planar support, while maintaining conventional peptide synthesis conditions, the selection of this polymer in this context is not compelling. In contrast, it even introduces disadvantages, such as, e.g., the greatly different salvation of the chains in different solvents. In addition, polyethylene is less mechanically stable than the preferred base polymer and the described films or other molded bodies that have been are generally not porous. Possible functionalizing is thus limited to the external surface (i.e., thick or thin grafted layer), which leads to a smaller charge capacity. A surface-selective functionalization is not assured. In fact, additional reactions (e.g., graft polymerization and homopolymerization) are triggered in the polyolefin film by the selection of γ-irradiation for initiating, particularly in the monomer/solvent system, but these reactions only reinforce the mechanical instability and cause a turbidity, which prevents application in assays.

Further, polypropylene membranes also functionalized with amino groups were described by Hudson et al. (WO 94/05394) in addition to the use of porous sintered plates, and a hydrophilic polymer (dextran, partially hydrolyzed chitin) is covalently coupled to these membranes by means of a spacer (PEG). The hydrophilic support materials used in small reactors (grid plates with holes) possess a uniform reactivity and are well suitable for screening purposes. Of course, the harsh primary modification via chromium oxidation is a particular disadvantage with respect to the use of porous supporting materials (with large specific surface and thus more sensitive morphology). Thus the membranes obviously can be handled only when they are fixed in the grid plates, i.e., as discontinuous supporting materials. In addition, the relatively expensive construction of the synthesis device leads to a strictly limited capacity and limited variability of the individual synthesis areas.

The patent of Koster et al. (EP 0 305,929) describes the synthesis of peptides and oligonucleotides on porous membrane polymers, on which reactive groups were produced on the surface by irradiation-initiated generation of radicals. The functionalization by means of very different (due to the selection of initiator and monomers) and strongly crosslinked polymer layers, however, may lead to nonuniform accessibility of the functional groups. Thus, these membranes appear unsuitable for SPOT synthesis. The suitability of large surfaces for synthesis and bioassays (which require stability and the same accessibility of all reactive groups) cannot be found here. In general, complications are to be expected in the case of solid phase synthesis of longer and/or more complex sequences.

Coassin et al. (WO 95/09176) reported on a polymer functionalization (polypropylene) with suitable reactive plasma (e.g., ammonia) in order to arrive at films and membranes as supports for the synthesis and sequencing of biomolecules. The functionalization, however, is accompanied by secondary reactions (oxidation), which clearly adversely affect the mechanical stability of the support. In addition, plasma functionalization, as is known, is not very chemoselective. The result is a small charge with reactive groups, since the modification is produced only on the surface and the flows of charge carriers and reactive species (in the case of reactive plasmas) must be minimized due to the degradation effect (see above).

Large-surface continuous supporting materials were described also by Eichler (DD 272,855 A1), Lebl et al. (EP 0 385,433 A2; EP 0 445,915 A1) and Okrongly et al. (EP 0 400,920). Whereas the first two patents refer to the modification of cellulose with the known disadvantages, in the latter, microtiter plates (polystyrene) are preferably functionalized on the surface for peptide synthesis. An advantageous monitoring of the course of reaction by means of UV spectroscopy, however, here contrasts with the disadvantages of a limited binding capacity as well as a limited mobility of the target molecules, each time due to the limitation of the functionalization to a simple polymer-like reaction at the non-porous polystyrene surface.

All of the systems of the prior art (functional supporting materials and synthesis conditions) have special serious disadvantages from the viewpoint of the requirements of SPOT synthesis, which prevent an effective application. In particular, a widespread application of SPOT synthesis for generating organic chemical substance libraries is impossible with the known continuous solid phase supporting materials. These disadvantages or limitations are overcome with the invention, which is described below.

The object is solved by a method for the synthesis of continuous polymeric solid phase supporting materials with spatially defined reaction sites that are separated from one another, comprising a supporting matrix and graft copolymer chains with reactive groups, which can react with organic compounds, with the following synthesis steps:

i.) Coating of the surface of the supporting matrix with a photoinitiator, which generates radicals at the polymer surface after UV excitation, by extraction of hydrogen and thus essentially without polymer degradation in the matrix,
   whereby the supporting matrix belongs to the group of at least one of the polymeric polyolefinic base polymers: polypropylene, polyethylene, polyvinylidene fluoride, polytetrafluoroethylene or crosslinked polystyrene, preferably polypropylene
   whereby the photoinitiator is a benzophenone derivative or ketone.

ii.) Exposure of the supporting matrix coated with photoinitiator with UV irradiation in the presence of an unsaturated functional monomer
   whereby the functional monomer contains a spacer group, which is covalently bound via an amide, ester, ether, disulfide or CC group with both a reactive group as well as with a group capable of polymerization.
   ($\alpha$) the spacer is an oligo or polyethylene glycol or a bond,
   ($\beta$) the polymerizable group is an acrylate, vinyl or allyl monomer,
   ($\gamma$) the reactive group, which can react with organic compounds, is a hydroxyl group, carboxyl group, amino group, mercapto group or a halogen group,
   ($\delta$) if necessary, a bond between the reactive group and the spacer or between the spacer and polymerizable group can be cleaved hydrolytically or by oxidation/reduction.

iii.) Formation of graft copolymer chains by covalent bonding of the polymerizable group of the functional monomer to the supporting matrix, whereby a monomer is first added to a radical of the polymeric supporting matrix and then other monomers are added to this [first] monomer in the sense of a polymerization.

iv.) Extraction of unreacted functional monomer and photoinitiator as well as of soluble secondary products.

DESCRIPTION OF THE INVENTION

The subject of the present invention is a method for the production of a new type of polymeric surface, on which organic substance libraries can be produced with the use of the SPOT synthesis concept, and their biological activity can be evaluated and read out directly on the supporting material.

According to the invention, surface-functionalized solid phase supporting materials are synthesized, which overcome the disadvantageous properties of current supporting materials indicated above in the description of the prior art or make possible completely alternative synthesis designs and techniques of combinatory synthesis by new functionalization strategies.

The good mechanical properties (stability) of the supporting material and a well-defined surface functionality are equally essential for the special requirements of SPOT synthesis. Of course, there are no homogeneous materials, which a priori combine these two properties. The example of chemically homogeneous cellulose, wherein new potential hydroxyl reactive groups continually are formed from the carbohydrate matrix upon application as a solid-state, hydroxyl-reactive supporting material, teaches rather that an optimal supporting material should be chemically heterogeneous. A supporting matrix, which essentially provides stability, with a chemically heterogeneous functional surface [is required].

Consequently, the heterogeneous functionalization of suitable polymetric matrix materials represents the most attractive synthesis path for obtaining new, continuous polymeric solid phase supporting materials that provide better performance. If this functionalization can also successfully lead to a surface selectivity, i.e., the chemical conversion of the matrix polymer can be limited to its surface, then supporting matrix and functional supporting surface can be optimized independently of one another.

The requirements for the supporting matrix result from the fact that a good, reliable manipulation before, during and after the multistep syntheses is a decisive factor for the success and quality of the syntheses and assays. On the other hand, a large specific surface in combination with suitable pore structure of the supporting matrix is the prerequisite for a high binding capacity per unit of surface. A sufficient dimensional stability (minimum swelling), however, must also be present, in order to be able to obtain a repositioning of the membrane during the syntheses and to obtain defined products in each spot and to read out the assay results without falsification. All of these requirements make it necessary that the supporting matrix must have an excellent mechanical, thermal and solvent stability under synthesis and assay conditions—despite the desired large specific surface.

The requirements for the functional surface with respect to synthesis are that the reactive groups be present in large quantity (at least up to 1 $\mu$mole/cm$^2$) and with good, constant accessibility (over all synthesis steps for the target molecules). This requires a large specific surface in combination with suitable pore structure of the supporting matarix (see above) as well as reactive groups at spacer groups or spacer chains, a good salvation of the functional groups and an optimal wetting of the external supporting surface (defined spots with minimal radial concentration gradients; no chromatography effects). In this way, a high product purity (per spot) and identical product quantities are obtained for all spots.

With respect to the assays, in addition, the accessibility and mobility of the synthesized molecules as well as minimal nonspecific interactions of the functional surface with the test proteins (minimum background for the readout of the results) are essential.

The production method will be robust, reproducible and flexible with respect to functionality and also the supporting matrix, as the case may be, as well as make possible a problem-free scaling-up to large surfaces. The new continuous polymeric solid phase supporting material, particularly the homogeneity and the stability of the supporting matrix, functional layer and its composite under synthesis and assay conditions are critical for the synthesis product.

Synthesis of the New Continuous Polymeric Solid Phase Supporting Materials

A polymer that is particularly well suitable as the supporting matrix is polypropylene, since it can be mechanically loaded and is chemically stable over broad regions of potential organic chemistry synthesis conditions (including a wide range of solvent and temperature conditions). A swelling barely occurs, except with very apolar solvents, which, however, play no role in synthesis. Polypropylene is available both in the form of thin, homogeneous, transparent films, as well as thick foils or plates, but also as a porous membrane with different pore morphologies and sizes. Depending on the target application (capacity desired—specific surface; mechanical flexibility), base materials for the synthesis of solid phase supporting materials can be selected from this spectrum. Preferably, macroporous flat membranes of polypropylene are selected as the supporting matrix (e.g., microfiltration membranes, produced by phase inversion and with sponge-like pore network with nominal pore size/mesh of 0.2 $\mu$m or filters with a spun and sintered nonwoven network structure with nominal pore size/mesh of 0.6 $\mu$m). Of course, other polymers, such as, e.g., polyethylene, polyvinylidene fluoride, crosslinked polystyrene or teflon with different morphologies may also be used. The supporting matrix may also be reinforced externally or internally by an additional inert supporting material or particles, fibers or networks of polymer, glass or metal.

In order to assure maximum stability under application conditions, a composite of the supporting matrix and a functional layer chemically anchored thereon is synthesized. The supporting matrix is preferably covalently functionalized by photoinitiated heterogeneous graft copolymerization with long graft polymer chains of functional monomers (strongly surface-selective with respect to the polypropylene matrix, but nearly uniform over the entire layer thickness). The new continuous polymeric solid phase supporting materials according to the invention for SPOT synthesis are obtained according to a method, which is comprised of the following essential steps:

i) Surface coating of the supporting matrix with a photoinitiator, which can generate radicals at the supporting surface after UV excitation (by hydrogen abstraction and thus without degradation of the matrix polymer);

ii) UV exposure of the coated supporting matrix in the presence of a functional monomer or monomer mixture with the formation of a functional layer, which consists of non-crosslinked functional graft copolymer chains anchored covalently to the matrix polymer (the UV exposure is preferably produced selectively, so that only the photoinitiator is excited);

iii) Extraction of unreacted monomers and photoinitiators as well as of soluble homopolymers or copolymers or photoinitator byproducts.

FIG. 1 shows schematically the production method for continuous planar solid phase supporting materials.

A sequential activation/initiation of graft copolymerization is also possible by first exposing the supporting matrix coated with photoinitiator according to i) in the presence of oxygen or with subsequent exposure in oxygen with the formation of supporting polymer peroxides and then the reaction with the monomer is thermally initiated. Other heterogeneous chemically initiated reactions may also be applied for initiating a graft copolymerization.

Benzophenone and structuraly related ketone derivatives are particularly suitable as the photoinitiator. Coating with a photoinitator in step i) may be conducted by dip-coating or impregnating from a solution in a solvent that does not dissolve the supporting polymer; however, it may also be produced directly prior to the graft copolymerization described in step ii) without additional process step, by adsorbing the photoinitator from a mixture of initiator, monomer or monomer mixture and, if necessary, solvent, on the supporting-material surface.

A structural constitution that can lead to a multiple number of surface functionalities in a modular manner according to a uniform reaction mechanism (heterogeneous graft copolymerization) is common to the monomers used:

Reactive group-spacer group-polymerizable group

Functional acrylates, methacrylates, acrylamides or methacrylamides are preferably used, but also other functional vinyl monomers and many others are suitable, in principle. Examples of reactive groups as an anchor for solid phase synthesis are hydroxyl or amino groups. Carboxyl or epoxy groups introduced by functional monomers may also be very easily used for this purpose (e.g., after "refunctionalizing" to amino groups). Oligo or polyethylene glycol chains are particularly suitable as spacer groups, since they can be well solvated in a similar way in many different solvents, guarantee a good mobility, and also improve biocompatibility. Cleavable linker structures may be, e.g., esters (in acrylates) or amides (in acrylamides), wherein the latter have an essentially better stability against hydrolysis and are preferred for solid phase syntheses under harsh organic chemical conditions. Hydroxy or amino (polyethylene glycol) methacrylates or methacrylamides are examples of monomers, that can be graft copolymerized to yield, supporting materials, which can be used directly with special advantages for SPOT synthesis. Supporting materials functionalized with graft polyacrylic acid can simply be "refunctionalized" with diamino-oligoethylene glycols to form hydrolysis-stable amino supporting materials.

The above-named functional monomers can be utilized in mixture with other functional monomers, and also with inert monomers, for the preparation of graft chains of copolymers. The latter inert monomers may be utilized for "dilution" of reactive groups at/in the solid phase supporting material or for adjusting the hydrophilic or hydrophobic nature or adjusting the charge (which is essential under certain circumstances for assay compatibility).

In the above-given supporting matrix, with corresponding homogeneous or porous structure and thus a smaller or larger specific surface, the degree of functionalization and thus the loading with reactive groups per unit of surface can be adjusted within a wide range (up to 10 $\mu$moles/cm$^2$) by the graft copolymerization conditions (photoinitiator coating, monomer concentration, exposure time). An increase in capacity is achieved by the graft copolymer chains in any case, compared with a polymer-like functionalized flat support surface. By selecting suitable conditions (light absorption of photoinitator and supporting matrix), uniform functionalizations of thick porous layers (with BP [benzophenone] in the case of PP [polypropylene] membranes up to 200 $\mu$m) are possible.

The preferably applied photofunctionalization permits, by a rapid and effective process, the reproducible and uniform functionalization of large continuous solid phase supporting material surfaces.

Syntheses on the New Continuous Polymeric Solid Phase Supporting Materials

By the selected production method, it is possible to generate primary reactive groups, preferably amino or hydroxyl groups, in large number (>1 $\mu$mole/cm$^2$) with good accessibility on a solid supporting matrix. Interestingly, this accessibility remains nearly constant even over a large number of synthesis cycles (10% decrease in load after approximately 10 synthesis cycles). The reason for this is the large specific surface in combination with the suitable pore structure of the supporting matrix of the supporting material (porous membrane) as well as a very good mobility of the reactive groups, caused by solvated graft copolymer chains and additional spacer groups. In addition, optimal wetting of the external support surface leads to defined spots with minimal deep-bed filtration effects and radial concentration gradients. Due to the constant excess of reagent caused thereby at each site of the wetting, a nearly constant product quality can be assured. Based on the homogeneity of the solid phase supporting material (identical number of equally accessible functionalities over the entire surface), identical quantities of product can be generated per spot. In addition, the reduced hydrophobia of the modified solid phase supporting material, in comparison to the supporting matrix, and in combination with the mobility of the bound substance induced by the spacer structures, leads to a good assay compatibility.

The polymeric solid phase supporting materials are further characterized by high chemical stability, i.e., resistance to strong acids, lyes, solvents as well as oxidizing and reducing reagents. In addition, the new polymeric solid phase supporting materials possess a high stability against physical influences such as temperature, ultrasound and microwave treatment, which results in the fact that the continuous surfaces show no swelling or only negligible swelling even after several reaction cycles. These properties permit a repeated, locally addressed pipetting of minimal volumes (10 nl) and in contrast to cellulose, an extensive variation of chemical reaction conditions.

The new continuous polymeric solid phase supporting materials can be prepared with a multiple number of linker constructs for taking up other molecules. Thus, in addition to acid-sensitive linkers (e.g., Rink linkers), UV-activatable photolinkers (e.g., 4-(methoxy-4-(2-Fmoc-aminoethyl)-5-nitrophenoxybutyric acid), base-labile linkers (e.g., HMBA linkers) or linker constructs that can be cleaved with aqueous buffer systems (e.g., imidazole linkers) can be used. These linkers can also be applied in parallel on the continuous solid phase supporting material by locally defined application of spots and can be utilized, e.g., for the synthesis of multiply or gradually cleavable products.

Although peptide substances of the same or better quality than in the case of conventionally used celluloses can be produced, in particular, a number of other possibilities result from the above-named properties of the new solid phase supporting materials for the synthesis of substance libraries produced by organic combinatory techniques. Since the new solid phase supporting materials according to the invention possess a high chemical and physical stability, their decisive advantages lie particularly in the combinatory synthesis of libraries of unnatural oligomers (e.g., peptoids, oligocarbamates, oligoureas, azatides, ketides, peptide sulfanamides, vinylogenic sulfonyl peptides) as well as small synthetic molecules (e.g., benzodiazepines, triazines, triazoles, hydantoins, cubans, xanthines, pyrrolidines, β-lactams, thiazolidones). Further, a key application lies in the parallel synthesis of chimeras (conjugates) of different synthetic (natural or unnatural) oligomers or small synthetic molecules with natural materials, such as, e.g., steroids or sugar molecules.

The use of continuous solid phase supporting materials, which have been produced according to the method of the invention is advantageous for the parallel and combinatory synthesis of support-bound or free compounds, which are synthesized by SPOT synthesis of activated synthesis building blocks at different reaction sites on the continuous solid phase supporting material.

A use according to the invention of the continuous solid phase supporting materials for the parallel and combinatory synthesis of proteins is preferred.

More preferred is a use according to the invention of the continuous solid phase supporting materials for solid phase synthesis, preferably SPOT synthesis, both as an array of identically or differently functionalized supporting materials or as a stack of identically or differently functionalized supporting materials for the synthesis of multiply or gradually cleavable compounds, whereby a quasi-threedimensional combinatory technique is possible by split (single sheets) and combine (stack) techniques with whole supports.

Still more preferred is the use according to the invention of the continuous solid phase supporting materials for the identification of molecules (ligands) of synthesized compounds, comprising the following steps:

Incubation with the ligand, removal of excess ligand by washing, detection of bound ligands by suitable methods such as: i) immunological detection, ii) detection of bound radioactively-labeled ligands, iii) fluorescence or chemoluminescence detection, iv) biosensory detection.

Most preferred is the use according to the invention of the continuous solid phase supporting materials for supporting enzymatic activities of synthesized compounds, comprising the following steps:

i.) Incubation with the enzyme, ii.) detection of enzymatic activity.

The invention will be described in more detail in the following based on examples, which explain the synthesis of the new continuous polymeric solid phase supporting materials, their application in SPOT synthesis of peptides and other organic chemistry molecules as well as of substance libraries comprised of peptides and other organic chemistry molecules, and application in analytical and screening systems. Of course, the invention is not limited to these concrete examples.

DEFINITIONS

Solid Phase Synthesis

Covalent coupling of molecules with an insoluble polymeric supporting material and subsequent reactions of the support-bound substances, whereby excessive reagents can be used and then separated by simple washing and filtering operations, and the target product remains bound to the polymeric supporting material until it is cleaved.

Functional Monomers

Molecules, which contain a polymerizable group, a spacer group and a reactive group and can form linear and/or branched polymer chains under the influence of a polymerization initiator.

Continuous Solid Phase Supporting Material

Planar material comprised of a supporting matrix (see below) with graft copolymer chains (see below) covalently anchored thereon.

Ligand

Molecule, which binds to the compound synthesized on the continuous solid phase supporting material and/or reacts with it chemically, and which can be a protein, enzyme, carbohydrate or glycoprotein, lipid or lipoprotein, a nucleic acid or a low-molecular compound.

Linker

Molecularly cleavable anchor molecule, which permits the cleavage of the synthesized target products from the solid phase supporting material Graft Copolymer Chains Linear and/or Branched Molecule Chains, Constructed from Functional Monomers (see below)

Photoinitiator

Produces radicals, which can react with a functional monomer, e.g., a benzophenone derivative or ketone, after coating the surface of a supporting polymer and excitation by means of UV irradiation by hydrogen abstraction from the supporting polymer.

Polymerizable Group

Reaction-capable multiple bond in functional monomers, e.g., an acrylate, vinyl or allyl group.

Radicals

Electrically neutral molecules, which possess a magnetic moment; a preferred reactivity is the addition to compounds, which contain reactive multiple bonds (polymerizable groups).

Reactive groups

Reactive chemical group (functionality) for covalent coupling reactions with other compounds, e.g., a hydroxyl group, carboxyl group, amino group, mercapto group or a halogen group.

Spacer Group

Molecular spacer between polymerizable group and reactive group in a functional molecule, e.g., an oligo or polyethylene glycol or a bond.

Spot

Is formed by the pipetting of reagents onto coherent continuous surfaces, whereby the pipetted volume defines the size of the SPOT and the number of possible SPOTs per unit of surface.

Spotting

Pipetting of Reagents onto Coherent Continuous Surfaces

SPOT synthesis

Solid phase synthesis concept in which SPOTs will be defined by pipetting of small drops of reagent onto a predefined array of reaction sites on a coherent continuous solid phase supporting material, which functions as the polymeric solid phase supporting material; these SPOTs represent microreactors, in which solid phase syntheses can occur, if solvents with low vapor pressure are used.

Supporting Matrix

Chemically and morphologically stable, planar material, which is comprised of polyolefin polymers (supporting polymers) such as polyethylene, polystyrene, polyvinylidene fluoride, polytetrafluoroethylene, but preferably polypropylene.

UV Excitation

Converts the photoinitiator into an Excited State without Exciting (Degrading) the Supporting Polymer

EXAMPLES OF EMBODIMENTS

Example 1

Synthesis of Continuous Polymeric Solid Phase Supporting Materials—Hydroxy-PEG-ester-PP Membranes with Various Spacer Lengths—Under Laboratory Conditions A PP membrane (Accurel 2E, Akzo; nom. pore diameter $d_p$=0.2 μm, layer thickness 150 μm; d=80 mm) is equilibrated by shaking for 2 h with a 100 mM solution of benzophenone (BP) in methanol. The membrane is removed from the solution and the surface is rapidly dried in air without de-wetting the inside of the pores. After this, the membrane is placed in a Petri dish (d=90 mm) on a filter paper impregnated with a part of the monomer solution (approximately 5 ml), attached with a glass ring (d=80 mm) and immediately overlayered with the remainder of the polymerization solution (a total of 20 ml of 50 g/l of PEGMA 306 or 78.5 g/l of PEGMA 526, each in water saturated with BP. The monomers—PEG methacryalates, wherein the number describes the average molecular weight—are products of Polysciences Europe GmbH, Eppelheim). The Petri dish is placed in a reactor, which is then sealed with a UV filter glass cover (cut-off 310 nm) and is flushed with nitrogen for at least 30 min. Subsequently UV exposure is produced—again under nitrogen flushing—for 30 min (HBO 350 deep UV; Hamamatsu, in an exposure apparatus of Oriel, 3 mW/cm$^2$). After another 15 minutes under nitrogen, the membrane is removed and then completely extracted with water, methanol and acetone. The degree of modification (DG) of the membrane is determined gravimetrically: DG (PEG MA 306)=1.12 mg/cm$^2$=3.5 $\mu$mole/cm$^2$; DG (PEGMA 526)=1.37 mg/cm$^2$=2.6 $\mu$mole/cm$^2$.

A further characterization is produced by FTIR-ATR spectroscopy, SEM, and measurement of membrane permeability.

Example 2

Synthesis of Continuous Polymeric Solid Phase Supporting Materials—Carboxyl-PP or Carboxyl-polyethylene (PE) Membranes—Under Laboratory Conditions A PP (Accurel 2E, Akzo; d$_p$=0.2 $\mu$m, layer thickness of 150 $\mu$m) or PE membrane (Celgard 2500, Hoechst-Celanese, d$_p$=0.2 $\mu$m, layer thickness of 25 $\mu$m) with a diameter of d=80 mm is equilibrated while shaking for 2 h with a 100 mM solution of BP in methanol. The membrane is removed from the solution and the surface is rapidly dried in air without de-wetting the inside of the pores. After this, the membrane is placed in a Petri dish (d=90 mm) on a filter paper impregnated with a portion of the monomer solution (approximately 5 ml), attached with a glass ring (d=80 mm) and immediately overlayered with the remainder of the monomer solution (a total of 20 ml of 10 g/l acrylic acid, AA, in water saturated with BP). The Petri dish is placed in a reactor, which is then sealed with a UV filter glass cover (cut-off 310 nm) and is rinsed for at least 30 min with nitrogen. It is then exposed—still under nitrogen rinsing—for 30 min (PP) or 15 min (PE) to UV (HBO 350 deep UV; 3 mW/cm$^2$). After another 15 min under nitrogen, the membrane is removed and then completely extracted with water and acetone. The degree of modification (DG) of the membrane is determined gravimetrically:

DG (PP)=220 $\mu$g/cm$^2$=3.1 $\mu$mole/cm$^2$;

DG (PE)=245 $\mu$g/cm$^2$=3.4 $\mu$mole/cm$^2$.

A further characterization is produced by FTIR-ATR spectroscopy, SEM, dye binding (toluidine blue), and measurement of the membrane permeability.

Example 3

Synthesis of Continuous Polymeric Solid Phase Supporting Materials—Hydroxy-amide-PP Membranes—Under Laboratory Conditions A PP membrane (Accurel 2E, Aczo; d$_p$=0.2 $\mu$m) with a diameter of d=80 mm is equilibrated with a 100 mM solution of BP in acetone for 2 h while shaking. The membrane is removed from the solution and the surface is rapidly dried in air without dewetting the inside of the pores. After this, the membrane is placed in a Petri dish (d=90 mm) on a filter paper impregnated with a portion of the polymerization solution, (approximately 5 ml), attached with a glass ring (d=80 mm) and immediately overlayered with the remainder of the polymerization solution (a total of 20 ml of 40 g/l of 2-hydroxypropylmethacrylamide, 2 HPMAm, in water saturated with BP; monomer of Polysciences). The Petri dish is placed in a reactor which is sealed with a UV filter glass cover (cut-off 310 nm) and is flushed with nitrogen for at least 30 min. Subsequently—still under nitrogen flushing—it is exposed to UV (HBO 350 DeepUV; 3 mW/cm$^2$) for 45 min. After another 50 min under nitrogen, the membrane is removed and then completely extracted with water and acetone. The determination of the degree of modification (DG) of the membrane is determined gravimetrically. DG=355 $\mu$g/cm$^2$=2.5 $\mu$moles/cm$^2$.

A further characterization is made by FTIR-ATR spectroscopy, SEM, dye binding (toluidine blue), and measurement of the membrane permeability.

Example 4

Synthesis of Continuous Polymeric Solid Phase Supporting Materials—Benzylchloride-PP Membranes—Under Laboratory Conditions A PP membrane (AN06, Millipore Corp: d$_p$=0.6 $\mu$m) with a diameter of d=80 mm is weighed and then equilibrated with a solution of BP in acetone (150 mM) for 2 h with shaking. The BP-coated, still moist membrane is placed in a Petri dish (d=90 mm) on a filter paper impregnated with a portion of the polymerization solution, attached with a glass ring (d=80 mm) and immediately overlayered with the remainder of the polymerization solution (a total of 20 ml of 20 g/l of vinyl benzyl chloride, VBC, emulsified in water saturated with BP with the addition of 7 g/l of the emulsifier bis [2-ethylhexyl]sulfosuccinate sodium salt at 10,000 rpm for 30 seconds with a Thurrax).

The Petri dish is shaken for 30 minutes and covered with a glass plate (deep UV filter, cut-off 310 nm). Exposure is made with half load in a UV dryer (Beltron-GmbH; 1 min UV exposure per passage through the exposure zone). Then the membrane is extracted with methanol for 1 h in a Soxhlet device and 1 h at 50° C. in water. After this, the modified membrane is dried and the degree of modification (DG) is determined gravimetrically. DG=1.5 mg/cm$^2$=9.8 $\mu$mol/cm$^2$. A further characterization is made by FTIR-ATR spectroscopy, SEM, dye binding (toluidine blue), and measurement of the membrane permeability.

Example 5

Synthesis of Continuous Polymeric Solid Phase Supporting Materials—Hydroxy-PEG-ester-PP Membranes—Under Technological Conditions A PP membrane (Accurel 2E, Akzo; d$_p$=0.2 $\mu$m or AN06, Millipore Corp.; d$_p$=0.6 $\mu$m) with a surface of 18 cm×26 cm is weighed and then shaken in a solution of BP in methanol or acetone for 2 h at room temperature. The still moist membrane coated with BP is placed in a dish containing 300 ml of monomer solution (PEGMA 526 in water saturated with BP) on filter paper and impregnated. The dish is covered with a glass plate (deep UV filter, cut-off 310 nm). Exposure is made at half-load in a UV dryer (Beltron GmbH; 1 min UV exposure per passage through the exposure zone). Then the membrane is extracted with methanol for 1 h in a Soxhlet apparatus and for 1 h at 50° C. in water. After this, the modified membrane is dried and the degree of modification is determined gravimetrically. The membrane is characterized analogously to that described in Example 1.

The degree of modification can be varied with the selection of synthesis conditions (photoinitiator coating, monomer concentration, exposure time) and can be adjusted for different supporting membrane types (for examples, see Table 1).

Example 6

Synthesis of Continuous Polymeric Solid Phase Supporting Materials—Carboxyl-PP Membranes—Under Technological Conditions A PP membrane (Accurel 2E, Akzo; d$_p$=0.2 $\mu$m, or AN06, Millipore Corp.; d=0.6 $\mu$m) with a surface of 18 cm×26 cm is weighed and then shaken in a solution of BP in methanol or acetone for 5 min at room temperature. The still moist membrane coated with BP is placed in a dish containing 300 ml of monomer solution (AA in water saturated with BP) on filter paper and impregnated. The dish is covered with a glass plate (deep UV filter, cut-off 310 nm). Exposure is made at half load in a UV dryer (Beltron GmbH; 1 min UV exposure per passage through the exposure zone). Then the membrane is extracted with methanol for 1 h in a Soxhlet apparatus and for 1 h at 50° C. in water. After this, the modified membrane is dried and the degree of modification is determined gravimetrically. The membrane is characterized analogously to that described in Example 2.

The degree of modification can be varied and adjusted for different types of supporting membranes by the selection of synthesis conditions (photoinitiator coating, monomer concentration, exposure time) (for examples, see Table 1).

TABLE 1

Technological synthesis conditions for selected hydroxy-PEG ester and carboxyl-PP membranes (membrane: 1 0.2 μm, Accurel 2E; 2 0.6 μm, AN06; UV exposure under half load with UV dryer, Beltron GmbH)

| Membrane | Photo-initiator coating | Monomer | Monomer (g/l) | Exposure (min) | DG (mg/cm²) | DG (μmole/cm²) |
|---|---|---|---|---|---|---|
| 1 | 150 mM BP/Acetone | PEGMA 526 | 78.5 | 15 | 1.28 | 2.4 |
| 1 | 150 mM BP/Acetone | AA | 23.3 | 10 | 0.48 | 6.8 |
| 1 | 150 mM BP/Acetone | AA | 50.0 | 10 | 0.64 | 9.0 |
| 2 | 100 mM BP/Acetone | PEGMA 526 | 78.5 | 10 | 0.19 | 0.36 |
| 2 | 100 mM BP/Acetone | PEGMA 526 | 100.0 | 10 | 0.34 | 0.65 |
| 2 | 100 mM BP/Acetone | AA | 50.0 | 10 | 0.13 | 1.8 |
| 2 | 150 mM BP/Acetone | AA | 50.0 | 5/5* | 0.17 | 2.4 |

*Membrane exposed on both sides

Example 7

Synthesis of Continuous Polymeric Solid Phase Supporting Materials—Chemical Derivatizing of a Carboxyl-PP Membrane (Amino Functionalization)

A piece of membrane (0.2 μm: from Example 6) of dimensions 18 cm×26 cm was treated in an instrument dish for 1 h with 80 ml of a 2 M solution of thionyl chloride in DCM. The solution was poured off and the still moist membrane was mediately reacted with 100 ml of a 30% solution of 4,7,10-trioxa-1,13-tridecanediamine in DCM (v/v). After 90 min, the solution was poured off and the membrane was washed (1×DCM, 5×methanol, 5 min each) and dried (diagram I)

Diagram I

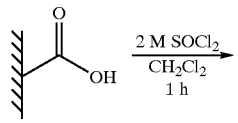

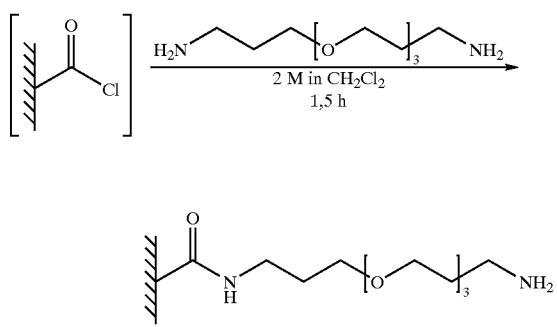

Example 8

Synthesis of Continuous Polymeric Solid Phase Supporting Materials—Chemical Derivatization of a Benzyl Chloride-PP Membrane (Amino Functionalization)

A piece of membrane (0.2 μm; from Example 4) of dimensions 5 cm×3 cm was treated in an instrument dish for 30 min with a 2.5 M solution of 4,7,10-trioxa-1,13-tridecanediamine in DCM (v/v) at room temperature. Then the solution was decanted and the membrane was washed (1×DCM, 3×DMF, 3×MeOH, 2×DCM, 5 min each) and dried (diagram II). Charge of 102 μmoles/cm². A piece of membrane (0.2 μm; from Example 4) of dimensions 5 cm×3 cm was treated in an instrument dish for 30 min with a 2.5 M solution of 4,7,10-trioxa-1,13-tridecanediamine in DCM (v/v) at 80° C. Then the solution was poured off and the membrane was washed (1×DCM, 3×DMF, 3×MeOH, 2×DCM, for 5 min each) and dried (Diagram II). Charge of 152 μmoles/cm².

Diagram II

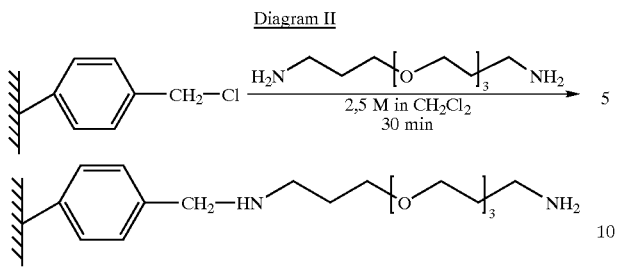

Example 9

Testing of Different Linker Systems to Hydroxy-PEG-ester PP Membranes

A hydroxy-PEG-ester PP membrane (0.2 μm, from Example 1) was refunctionalized by successive spotting of 1 μl of a 0.6 M NMI solution in NMP and 1 μl of a 0.6 M solution of Fmoc-βAla-F in NMP (amino: reaction time 2×30 min). After complete cleavage of the Fmoc protective groups (bathing of the membrane in 20% piperidine/DMF, 2×15 min) and subsequent washing with DMF (2×), methanol (2×) and DCM (2×) and drying in air, the following activated linker molecules were spotted on the free amino functions stained with bromophenol blue:

A) 2 μl of 0.6 M Rink linker (p-[(RS)-μ[1-(9H-fluoren-9-yl) -methoxyformamido]-2-4-dimethoxybenzo] phenoxy acetic acid) in NMP (preactivated for 5 min with 1 eq. of TBTU and 2 eqs. of DIEA).

B) 2 μl of 0.6 M imidazole linker in NMP (preactivated for 5 min with 1 eq. of TPTU and 1 eq. of DIEA)

C) 2 μl of 0.6 M aminoethyl photolinker 4-[2-methoxy-4-(1-Fmoc-aminoethyl)-5-nitrophenoxy]butyric acid) in NMP (preactivated for 5 min with 1 eq. of TBTU and 2 eqs. of DIEA)

D) 2 μl of 0.6 M hydroxyethyl photolinker 4-[2-methoxy-4-(hydroxyethyl)-5-nitrophenoxy]butyric acid) in NMP (preactivated for 5 min with 1 eq. of TBTU and 1 eq. of DIEA).

In all cases, the reaction time amounted to 2×30 min. After cleavage of the Fmoc groups, the model peptide (Ac-Leu-Lys-Tyr-βAla) was constructed by means of Fmoc-amino acid-OPfp esters [pentafluorophenyl esters] (2 μl, 0.3 M in NMP, 2×15 min) under spot synthesis conditions. In addition to synthesis on linker systems, a synthesis was also directly conducted on the βAla-modified membrane. Subsequent to spotting the first amino acid, the membrane was acetylated in order to define the spot size (Ac$_2$O, DIEA, DMF; 1:2:7; 30 min). After cleavage of the last Fmoc group, the peptides were again acetylated. The side-chain protective groups were de-blocked by means of 5% H$_2$O in TFA (2 h) in the case of the imidazole linker, the photolinker and direct synthesis without linker. Then the peptides were cleaved as follows:

Rink linker: 2 h, 95% TFA; 5% H$_2$O
Imidazole linker: 1 h phosphate buffer, pH: 7.4
Photolinker (C+D): cleavage in the dry state by means of UV irradiation: 2 h, 365 nm.

After evaporating the TFA and taking up the adhesively bound peptides in 50% ACN/H$_2$O, the quality of the products was monitored by means of HPLC and mass spectrometry analysis. All of the linkers that were applied onto the new solid phase supporting materials made possible the isolation of the products with high HPLC purity (>85%).

Example 10

Comparative Synthesis of Peptides on Conventionally Used Cellulose and Hydroxy-PEG-ester PP Membranes The cellulose and the hydroxy-PEG-ester PP membranes (0.2 μm, from Example 1) were acylated with Fmoc-βAla-F/NMI in NMP and, after cleavage of the Fmoc group (20% piperidine/DMF, 20 min), were modified with the photolyzable linker 4-2-[methoxy-4-(1-Fmoc-aminoethyl)-5-nitrophenoxy]butyric acid). The following peptides of different chain lengths were constructed stepwise under identical conditions by means of Fmoc-protected amino acid-pentafluorophenyl esters (2 μl of a 0.3 M solution in NMP, double coupling, 2×15 min):

The N-terminal amino function was acetylated and the side chain protective groups were cleaved for 2.5 h by means of 5% H$_2$O, 5% phenol, and 2.5% TIPS in TFA. After abundant washing with DCM and methanol, the membranes were dried and the peptides were cleaved from the surface by irradiation with UV light (2 h, 365 nm). The compounds adhesively bound on the membrane, after punching out and transferring to microtiter plates, could be stripped by means of buffer and introduced to HPLC/MS analysis.

In all cases, the peptides produced on the hydroxy-PEG-ester-PP membrane possess a higher product purity than those synthesized on conventional cellulose, as is demonstrated by the analytical profiles of the test.

Example 11

Synthesis of Small Organic Molecules: 1,3,5-triazine library 2.3 μl of a 0.5 M solution of p[(R,S)-a*-[1-(9H-fluoren-9-yl) methoxyformamido]-2,4-dimethoxybenzyl]phenoxy acetic acid (Rink linker), TBTU (1 eq.) and DIEA (2 eqs.; preactivation time: 5 min) were spotted onto an amino-derivatized carboxyl-PP membrane (see Example 7) at distances of 0.8 to 1 cm. After 15 min, the spotting was repeated. After another 15 min, the membrane was washed twice for 5 min with MeOH and twice for 10 min with DCM. Then the spot procedure was repeated. Loads of approximately 700 nmoles/cm$^2$ were

*sic; αor μ?—Trans. note. obtained according to Fmoc quantification, which corresponded to >90% of the functionality density of the amino-derivatized polypropylene membrane.

The membrane derivatized with Rink linker (100 cm$^2$; 96 spots) was bathed twice for 25 min in 75 ml of 25% piperidine solution in DMF and then twice for 10 min each time with 50 ml each of DMF, MeOH and DCM. For acylation of the free amino function, a 0.6 M solution of the amino acid with one equivalent of TBTU and 2 equivalents of DIEA in DMF was spotted onto the membrane (2 μl per spot). After 15 min, the procedure was repeated. After the reaction time had terminated, the membrane was washed twice for 10 min each time with 50 ml each of DMF, MeOH and DCM. The amino function was again de-protected by bathing the membrane twice for 25 min in 75 ml of a 25% piperidine solution in DMF and subsequent washing (2× each, 10 min, with 50 ml each of DMF, MeOH and DCM).

The amino acid-derivatized membrane was then poured over a 3 M solution of cyanuric chloride containing 3% DABCO in DCM and shaken up for 15 min at 4° C. and for 10 min at room temperature. Then the membrane was washed 3× with 50 ml of DCM, 2× with ACN (50 ml) and 2× with 50 ml of DCM for 10 min each time.

2 μl of a 60% solution of primary or secondary amines (NHR$_2$R$_3$) in NMP were spotted onto the previously derivatized membrane and left to react in the closed vessel for 25 min at room temperature, for the substitution of chlorine atoms on the solid-phase-bound 1,3,5-triazine derivative. Then the membrane was washed 3 times with 75 ml each time of DMF (20 min), twice with 75 ml each time of MeOH (20 min) and 3 times with 75 ml each time of DCM (15 min). The primary or secondary amine was spotted onto the air-dried membrane in a glass dish for the substitution of the still remaining chlorine atoms (2 μl of an 80% solution in NMP) and the membrane was heated for 3 min in a microwave. The excess amines were removed from the membrane with DMF (3×, 75 ml each time, 20 min), 0.1% aqueous acetic acid (75 ml, 20 min), MeOH (three times*, acetic acid (75 ml, 20 min), MeOH (3 times with 75 ml each time, 20 min) and DCM (3 times with 75 ml each time, 20 min).

*sic—"MeOH (three times" may be an error here—Trans. note.

After punching out and transferring to microtiter plates, the molecules were cleaved by means of 150 μl of 90% TFA/DCM per spot (35 min, 30° C.). After blowing off the TFA in the nitrogen current, the substances were taken up in appropriate buffer systems and analyzed.

Example 12

Synthesis of Small Organic Molecules: Peptoid (N-benzyl-N-[butyl(carbamoylmethylcarbamoylmethyl)carbamoylmethyl-2-[piperdin-1-yl]acetamide).

An amine-derivatized carboxyl-PP membrane (see Example 7; compare Example 11) was treated with 30 ml of a 0.3 M solution of Fmoc-glycine in DMF (30 min), after the solution had been preactivated with 1 eq. of TBTU and 2 eqs. of DIEA. After washing the membrane and cleaving the protective groups (3×DMF, 5 min each, 1×20% piperidine/DMF, 20 min, 5×DMF, 5 min each time), the membrane was again reacted with 30 ml of a freshly prepared solution of pre-activated Fmoc-glycine. After 30 min of reaction time and washing the membrane with DMF (3×5 min), 4 samples were punched out of the membrane (0.23 cm$^2$), in order to determine the chemically achieved degree of coating of the membrane. For this purpose, the samples were mixed individually with precisely 1.00 ml of a 20% solution of piperidine in DMF and the UV absorption was measured at 301 nm. A degree of coating of 0.45 μmole/cm$^2$ was achieved (corresponds to 10% of the gravimetrically determined load).

The membrane provided with 2 glycine spacers was then modified with Rink linker system as described in Example 9 and unreacted amino functions were acetylated (Ac$_2$O, DIEA, DCM; 1:2:7). The amino function released after cleavage of the Fmoc-protected group, washing and drying, was amidated by pipetting of 0.2 μl of a 0.3 M Fmoc-glycine-pentafluorophenyl ester solution in NMP (3×15 min). The membrane was washed as described above and the Fmoc group was cleaved.

The amino function was then acylated by pipetting of 0.2 μl of a 1 M solution of bromoacetic acid-2,4-dinitrophenyl ester in NMP (3×15 min). After washing by means of DMF (3×, 5 min) and methanol (3×, 5 min) and subsequent drying in air, the bromine was substituted nucleophilically by spotting of 0.2 μl of n-butylamine (5 M in NMP, 3×15 min). After washing (3×5 min DMF, 3×5 min methanol) and drying in air, two additional synthesis cycles were conducted, which differed by the nature of the amine that was used (cycle 2: n-butylamine; cycle 4: piperidine).

The punched-out spots were cleaved by means of TFA as described in Example 9 and the products were isolated and analyzed. All of the investigated products showed the expected identity with a HPLC purity of >70%.

Example 13

Synthesis of Oligomeric Hybrids of Peptides and Peptoids (Peptomers)

2.5 μl of a 0.6 M solution of 4-(methoxy-4-(2-Fmoc-aminoethyl)-5-nitrophenoxy)butyric acid (photolabile amide linker), TBTU (1 eq.) and DIEA (2 eqs.; preactivation time: 5 min) were spotted onto an amino-derivatized carboxyl-PP membrane (see Example 7) at distances of 1.0 to 1.5 cm. Spotting was repeated after 15 min. After another 15 min, the membrane was washed 3 times for 5 min with DMF, twice for 5 min with MeOH and twice for 10 min with DCM. Then the SPOT procedure was repeated. Loads of approximately 700 nmoles/cm$^2$ were obtained according to Fmoc quantification, which corresponded to approximately 90% of the functionality density of the amino-derivatized polypropylene membrane.

The amino functions that did not react with the photolabile amide linker are acetylated (Ac$_2$O, DIEA, DCM; 1:2:7; 30 min) and then washed 3 times for 5 min in DMF. The Fmoc protective group of the linker is cleaved by bathing the membrane twice for 25 min in 75 ml of 25% piperidine in DMF. Then the membrane is washed 2 times for 10 min each time with 50 ml each of DMF, MeOH and DCM.

Fmoc-amino acid-pentafluorophenyl ester (0.3 M in NMP; amino acid spots) or bromoacetic acid-2,4-dinitrophenylester (1.0 M in NMP; peptoid spots) are spotted onto the membrane for the acylation of the released linker amino functions (2.5 μper spot). This procedure is repeated a total of 3 times for 15 min each time. After the reaction time has terminated, the membrane is washed twice for 10 min each time with 50 ml each of DMF, MeOH and DCM. The Fmoc-amino functions of the amino acid spots are deprotected by triple spotting for 15 min with 50% piperidine/NMP solution. At the same time, the substitution of bromine functions of the peptoid spots is conducted by spotting of 1 to 5 molar solutions of primary and secondary amines in DMF, NMP, DMSO, dimethyl acetamide or water. After the end of the reaction time, the membrane is washed twice for 10 min each time with 50 ml each of DMF, MeOH and DCM.

The acylation of the primary amine functions (amino acid spots) and secondary amine functions (peptoid spots) is conducted either by spotting (3×15 min) of 0.3 M solutions of Fmoc-amino acid-pentafluorophenyl esters in NMP (amino acid spots), 0.3 M Fmoc-amino acid-anhydrides in NMP (peptoid spots) or of a 1.0 M solution of bromoacetic acid-2,4-dinitrophenyl ester in NMP (amino acid and peptoid spots). After the reaction time has terminated, the membrane is washed twice for 10 min each time with 50 ml each of DMF, MeOH and DCM. Then the synthesis is continued as described above.

The Fmoc-amino acid-anhydrides are generated from the Fmoc-amino acids (0.6 M Fmoc-amino acid in NMP; addition of 0.5 eq. of DIC; preactivation: 30 min).

After synthesis is concluded, the side-chain protective groups are cleaved (5% H$_2$O, 5% phenol, 2.5% TIPS in TFA). After abundant washing with DCM and methanol, the membranes are dried and the peptides are cleaved from the membrane by irradiation with UV light (365 nm, 7 mW/cm$^2$, 90 min).

The adhesively bound compounds could be stripped by means of buffer after punching out and transferring to microtiter plates and introduced to HPLC/MS analysis. The different peptomers showed relatively high product qualities whereby the maximum peak each time corresponded to the target mass of the desired product.

Example 14

Investigations on Biocompatibility: Antibody Binding Study on Polymer Membranes

The epitopes Ac-Leu-Pro-Asn-Met-Leu-Arg-Asp-Leu-Arg-Asp-Ala-Phe-Ser-Arg-Val-βAla (mAb CB/RS/13-epitope); Ac-Ile-Phe-Ile-Asn-Tyr-Ile-Glu-Ala-Tyr-Met-Thr-Met-Lys-Ile-Arg-βAla (mAb CB/RS/11-epitope); Ac-Val-Val-Ser-His-Phe-Asn -Asp-βAla (mAb Tab2-epitope) and the nonspecific test sequence Ac-His-Val -Asn-Ser-Leu-Gly-Glu-Asn-Leu-Lys-Thr-Leu-Arg-Leu-Arg-βAla were synthesized under the conditions of spot synthesis (see Example 10), and each time parallelly on conventional cellulose and polypropylene membranes.

After cleavage of the side-chain protective groups (2.5 h; 94% TFA, 3% TIPS, 2% $H_2O$, 1% phenol) and washing with DCM (3×), DMF (4×) and methanol (2×), the methanol-moistened membrane was washed 3×10 min with Tris buffered saline (T-TBS), pH 8.0 After this, the membrane was incubated with blocking buffer (Boehringer Mannheim, Mannheim, Germany) for over 2 h and then washed 3×10 min with T-TBS buffer (pH 8.0). The thus-treated membrane was then incubated for more than 1 h with peroxidase (POD)-labeled polyclonal anti-mouse IgG antibody (0.1 μg/ml of blocking buffer). The antibody solution was discarded and the membrane was washed 3×10 min with T-TBS buffer (TBS/Tween(R)®20, pH 8.0). Then the polymer membrane was rinsed with a chemoluminescent substrate (Boehringer Mannheim) and enzyme activity was characterized with the Lumi Imager (Boehringer Mannheim).

| | |
|---|---|
| λ | Lambda (wavelength) |
| AA | acrylic acid |
| Ac | acetyl |
| Ac$_2$O | acetic anhydride |
| ACN | acetonitrile |
| ATR | attenuated total reflection |
| BP | benzophenone |
| Chem. Rev. | Chemical Reviews |
| d | diameter |
| DABCO | diazabicycloundecane |
| DCM | dichloromethane |
| DIC | diisopropylcarbodiimide |
| DIEA | diisopropylethylamine |
| DMF | N,N'-dimethylformamide |
| DMSO | dimethyl sulfoxide |
| DNA | deoxyribonucleic acid |
| d$_p$ | pore diameter |
| ELISA | enzyme linked immunosorbent assay |
| Eq. | equivalent |
| Fmoc | 9-fluorenylmethyloxycarbonyl- |
| Fmoc-βAla-F | N-(9-fluorenylmethyloxycarbonyl)-β-alanine fluoride |
| FTIR | Fourier Transform Infrared Spectroscopy |
| h | hours |
| HMBA | 4-hydroxymethylbenzoic acid |
| HPLC | high performance liquid chromatography |
| i.w. | essentially |
| J. Am. Chem. Soc. | Journal of the American Chemical Society |
| Leu | leucine |
| Lys | lysine |
| M | moles per liter |
| MeOH | methanol |
| mM | millimolar |
| mm | millimeter |

-continued

| | |
|---|---|
| MS | mass spectrometry |
| NMI | N-methylimadazole |
| NMP | N-methylpyrrolidone |
| OPfp | pentafluorophenyl ester |
| PE | polyethylene |
| PEG | polyethylene glycol |
| pH | negative common logarithm of the hydrogen ion concentration |
| PP | polypropylene |
| prim | primary |
| proz | percent |
| REM [SEM] | scanning electron microscope |
| RNA | ribonucleic acid |
| sec. | secondary |
| βAla | beta-alanine |
| TBTU | 2-(1H-benzotriazol-1-yl)-1,1,3,3-tetramethyluronium tetrafluoroborate |
| Tetrahedron Lett. | Tetrahedron Letters |
| TFA | trifluoroacetic acid |
| TIPS | triisopropylsilane |
| Tyr | tyrosine |
| RPM | revolutions per minute |
| UV | ultraviolet |
| v/v | volume by volume |

What is claimed is:

1. A method for the parallel and combinatory synthesis of compounds comprising the steps of:

preparing a continuous polymeric solid phase supporting material comprising a matrix of a supporting polymeric material and graft copolymer chains covalently bound to the supporting matrix, the graft copolymer chains having reactive groups being able to react with organic compounds, thereby forming spatially defined reaction sites, and sequential spotting of synthesis building blocks or reagents at the various reaction sites on the continuous solid phase supporting material to yield a library of compounds bound to the solid phase supporting material, whereby each reaction site on the continuous solid phase supporting material determines the composition of the synthesized compound, which is bound directly on the supporting matrix via the reactive groups of the graft polymer chain, wherein said preparing step comprises coating the supporting material with a photoinitiator that, after UV excitation generates radicals at the surface of the supporting polymeric materials, and exposing the coated supporting polymeric material to UV radiation in the presence of at least one unsaturated functional monomer to form graft copolymer chains.

2. The method as claimed in claim 1 wherein said bound compounds are proteins.

3. The method as claimed in claim 1 wherein said bound compounds are selected from the group consisting of peptides, peptoids, peptomers, oligocarbamates, oligoureas, azatides, ketides, peptide-sulfonamides, vinylogenic sulfonyl peptides, DNAs, and peptide nucleic acids.

4. The method as claimed in claim 1 wherein said bound compounds are small synthetic molecules.

5. The method as claimed in claim 4 wherein said small synthetic molecules are benzodiazepines, triazines, triazoles, hydantoins, cubans, xanthines, pyrrolidones, β-lactams, thiazolidones, isoquinolines, and diketopiperazines.

6. The method as claimed in claim 1 wherein said bound compounds are compounds synthesized by introducing variable groups on a central core structure by sequential spotting.

7. The method as claimed in claim 1 wherein said bound compounds are chimeras of (i) a member selected from the group consisting of synthetic oligomers and small synthetic molecules, and (ii) natural materials.

8. The method as claimed in claim 1 wherein said supporting polymeric material is selected from the group consisting of polypropylene, polyethylene, polyvinylidene fluoride, polytetrafluoroethylene and a crosslinked polystyrene.

9. The method as claimed in claim 1 wherein said photoinitiator is selected from the group consisting of benzophenone, a benzophenone derivative and a ketone.

10. The method as claimed in claim 1 wherein said unsaturated functional monomer comprises a spacer group, a reactive group and a group capable of polymerization, said spacer group being covalently bound to each of said reactive group and said group capable of polymerization.

11. The method as claimed in claim 10 wherein said spacer group is covalently bound to each of said reactive group and said group capable of polymerization by a member selected from the group consisting of an amide, an ester, an ether, a disulfide or a CC group.

12. The method as claimed in claim 11 wherein said spacer group is an oligo or polyethylene glycol.

13. The method as claimed in claim 12 wherein said unsaturated functional monomer comprises a reactive group and a group capable of polymerization.

14. The method as claimed in claim 13 wherein said reactive group is bonded directly to said group capable of polymerization.

15. The method as claimed in claim 13 wherein said group capable of polymerization is selected from an acrylate, a vinyl and an allyl.

16. The method as claimed in claim 13 wherein said reactive group is selected from a hydroxyl group, a carboxyl group, an amino group, a mercapto group and a halogen group.

17. The method as claimed in claim 10 further comprising, after said spotting step, the step of cleaving the bond between the spacer group and one of the reactive group and the group capable of polymerization, thereby yielding free compounds.

18. The method as claimed in claim 17 wherein said cleaving step is performed hydrolytically.

19. The method as claimed in claim 17 wherein said cleaving step is performed by oxidation/reduction.

20. The method as claimed in claim 1 wherein said preparing step is performed so as to generate arrays of identically or differently functionalized supporting materials or stacks of identically or differently functionalized supporting materials for the synthesis of multiply or gradually cleavable compounds.

21. A method for identifying ligands, comprising the following steps:

incubation of the compounds bound to the continuous solid phase supporting material of claim 2 with the ligand, removal of excess ligand by washing and detection of bound ligand by a technique selected from the group consisting of i) immunological detection, ii) detection of bound radioactively-labeled ligand, iii) fluorescence or chemoluminescence detection, and iv) biosensory detection.

22. A method for investigating enzymatic activities comprising the following steps:

i.) incubation of the compounds bound to the continuous solid phase supporting material as claimed in claim 1 with the enzyme; and ii.) detection of enzymatic activity.

* * * * *